(12) United States Patent
Ma (10) Patent No.: US 6,878,951 B2
(45) Date of Patent: Apr. 12, 2005

(54) HELICAL ELECTRON BEAM GENERATING DEVICE AND METHOD OF USE

(75) Inventor: Lijun Ma, Ellicott City, MD (US)

(73) Assignee: University of Maryland, Baltimore, MD (US)

( * ) Notice: Subject to any disclaimer, the term of this patent is extended or adjusted under 35 U.S.C. 154(b) by 0 days.

(21) Appl. No.: 10/259,561

(22) Filed: Sep. 30, 2002

(65) Prior Publication Data

US 2004/0079899 A1 Apr. 29, 2004

Related U.S. Application Data

(63) Continuation-in-part of application No. PCT/US01/10587, filed on Mar. 30, 2001.
(60) Provisional application No. 60/193,474, filed on Mar. 31, 2000.

(51) Int. Cl.[7] .................................................. G21K 1/02
(52) U.S. Cl. .............................. 250/505.1; 250/492.1; 315/505; 315/500
(58) Field of Search ........................... 250/492.1, 505.1

(56) References Cited

U.S. PATENT DOCUMENTS

| | | |
|---|---|---|
| 4,093,891 A | 6/1978 | Christie et al. |
| 4,200,820 A | 4/1980 | Symons |
| 4,507,586 A | 3/1985 | Correll |
| 4,571,524 A | 2/1986 | Mourier |
| 4,812,707 A | 3/1989 | Correll |
| 5,339,347 A | 8/1994 | Slatkin et al. |
| 5,510,670 A | 4/1996 | Osborne et al. |
| 5,974,112 A | 10/1999 | Reiffel |
| 6,060,833 A | 5/2000 | Velazco |
| 6,127,688 A * | 10/2000 | Wu .......................... 250/505.1 |
| 6,433,494 B1 * | 8/2002 | Kulish et al. ................ 315/500 |

* cited by examiner

*Primary Examiner*—Nikita Wells
*Assistant Examiner*—Phillip A Johnston
(74) *Attorney, Agent, or Firm*—Sughrue Mion, PLLC (57) ABSTRACT

A device for generating helical electron beams that can be used for radiation therapy is disclosed. The device contains a tertiary collimating cone that can be attached to a gantry of a linear accelerator or placed directly below the gantry. The tertiary collimating cone has a dynamic energy compensator and a magnetic electron collimator to modify the energy of electrons and to generate a helical trajectory. A multileaf collimator may be present within the tertiary collimating cone. A computer coordinates the movements of various components. The helical electron beam produced by this device can be targeted to tumors better and safer and reduce the amount of radiation hitting normal tissue than current devices.

34 Claims, 6 Drawing Sheets

Figure 3 Percentage depth dose curves for 15 MeV electrons subject to magnetic fields with strengths of 20 kG (dashed) and 50 kG (dotted). The solid curve is the PDD for no applied field.

Figure 4 Dose enhancement for magetic fields with strengths of 20 kG (dashed) and 50 kG (dotted). Dose enhancement is defined as the Dose(depth, B) / Dose(depth, B=0).

Figure 5. Computed isodose dose distribution for energy and intensity modulated electron beam for a chest wall treatment. The beam aims to cover the chest wall with 90% isodoseline and spare the heart with 40% isodose line coverage.

HELICAL ELECTRON BEAM GENERATING DEVICE AND METHOD OF USE

This is a Continuation-in-Part of Application No. PCT/US01/10587, filed Mar. 30, 2001, which claims benefit of priority to U.S. patent application Ser. No. 60/193,474 filed on Mar. 31, 2000.

The research for this invention was sponsored by the U.S. Army, grant number BC 99087. The U.S. government has certain rights to this invention.

BACKGROUND OF THE INVENTION

1. Field of Invention

This invention relates to a device for radiation treatment for cancer and the method thereof. It more specifically relates to a device to generate helical electron beams for radiation therapy for tumors and the method of irradiating tumors with a helical electron beam.

2. Description of the Related Art

Radiation therapy has been effective for managing early stage (stage I–II) breast cancers following breast conservation surgery (BCS). More recent studies have indicated that radiation therapy also improves survival rate for late stage (stage III–IV) breast cancer patients. However, the high risk of cardiac or pulmonary complications often compromises the treatment of these patients using conventional radiation therapy techniques.

Conventional photon beams have been used successfully for treating early stage breast cancer treatment. It is now widely accepted that radiation therapy following breast conservation therapy is as effective as mastectomy for early breast cancers [1–9]. Radiation therapy has also been used for managing late-stage breast cancer patients [10–16]. More recent studies have found that radiation therapy improves survival for a subgroup of patients with late-stage breast cancer [15–16].

Conventional radiation therapy techniques use two opposing tangential photon beams to treat the whole breast. The advantage of photon beam is that it has sharp beam delineation and high penetrating power. The disadvantages of photon beam treatment are as follows:

(1) Limited beam setup options. Patient geometry may sometimes include excessive heart or lung volume for irradiation.

(2) Unable to treat internal mammary nodes because of the proximity of the node chains to the heart.

(3) Potential high scatter dose to the contralateral breast.

(4) Patient breathing motion may introduce accidental irradiation of large volume of heart or lung.

These restrictions especially the first one have restricted the use of photon beam radiation therapy for advanced breast cancer treatment. Several clinical studies have reported significant rate of cardiac or pulmonary toxicity associated with the conventional photon beam techniques [17–27]. High risk of irradiating the heart or lung becomes critical for post-mastectomy patients when they receive chest wall or internal mammary node treatments [20–21]. The limitation of photon beam breast treatment is evident from a recent study that compares the photon Intensity Modulation Radiotherapy (IMRT) technique with the conventional radiation therapy techniques for breast cancer treatment [28]. The results of the study show that IMRT presents almost no advantage over the conventional techniques for whole breast treatment. This result implies that there may be not much room in improving the existing techniques for photon beam treatment of breast cancers.

Electron beams, on the other hand, offer attractive features for breast cancer treatment. First, breast tumors are relatively shallow that could be penetrated by electrons of 18–20 MeV. These electron beams are already available for most medical accelerators. Second, the electron beam exhibits fast fall-off near the end of its range of travel. These features enable treatment of the internal mammary nodes or the chest wall region while sparing the heart or lung underneath. Because the anterior-posterior direction of the breathing motion coincides with the beam-on direction, the simple treatment setup reduces the possibility of over irradiation of the heart or lung due to patient breathing motion. This is analogous to the treatment of lung cancer patients where direct anterior-posterior setup has been found to be the most reliable and effective treatment method [29]. In comparison, electron beam would overcome all the above listed disadvantages associated with the photon beam treatment. One major disadvantage of electron beams is their excessive scatter and beam penumbra.

Recent rapid developments in computer controlled beam delivery systems have become a driving force in developing intensity modulation radiotherapy (IMRT) using high-energy photon beam [30–49]. The technology has become mature enough that several clinical trials are near their completion [48–49].

Because of the high cost and few locations that can handle high-energy photon beam radiation therapy, it would be useful to have a different approach to reduce radiation to non-cancerous tissue while increasing the radiation to cancerous tissue. One approach would be to use electron beams. But the problem with electron beams is their tendency to scatter.

If one could reduce the problems associated with electron beam radiation, one would be able to develop intensity modulated electron beam for Avoidance Radiation Therapy (ART). The idea of ART has been applied to almost every aspect of radiation therapy where a tumor dose is typically limited by the tolerance of normal tissue structures. If normal tissue dose could be significantly reduced or avoided, then the complication rate would be reduced. This reduction in radiation of normal tissue would permit dose escalation to achieve better local control of the tumor and improves the prospects for patient survival [50]. Several promising beam modulation techniques have been proposed for ART treatment using electron beams [51–57].

One approach is using finely collimated beams scanning across the entire treatment area using more sophisticated beam transport systems such as those used in the Racetrack Microtron [51–54]. This approach requires significant modification of the design for most clinical linear accelerators; and thus is not feasible. Another approach is to simply use the photon beam multileaf collimator system (MLC) for electron-beam intensity modulation [57]. This approach has not yet solved the problem the excessive electron beam scatter effects.

There have been several theoretical studies and preliminary experiments exploring the use of static magnetic fields in shaping clinical electron beams [58–63]. None of these studies and experiments has proven to be successful yet.

Several unique beam delivery algorithms using computer controlled MLC systems have been recently developed for beam delivery optimization and verification [39–47]. Conventional three-dimensional pencil beam algorithm is a fast and practical method used in most clinical treatment planning systems [64–65]. A more time-consuming Monte Carlo method has also been recently developed particularly for various heterogeneous cases [66–68]. These algorithms could be used or modified for an improved electron beam radiation system.

BRIEF SUMMARY OF THE INVENTION

It is an object of this invention to have a device for achieving intensity, energy and spatially modulated Avoidance Radiation Therapy for treatment of cancer. It is a further object of this invention that this device could be directly attached to the gantry of the medical accelerator similar to a conventional electron cone or can be attached to a moveable platform or stand and detachably secured into position during radiation therapy. It is a further object of this invention that the device use a radiation source inside a linear accelerator to generate electrons and one or more magnets with the magnetic field in the same direction as the path of the electrons to cause the electrons to travel in a helical trajectory parallel to the magnetic field.

It is object of this invention to have a tertiary collimating cone with a dynamic energy compensator and a magnetic electron collimator which, when used in conjunction with a linear accelerator, induces electrons from the linear accelerator to travel in a helical pathway. It is a further object of this invention that the magnetic field of the magnetic electron collimator is parallel to the direction of the travel of the electrons. It is a further object that this device can be used to irradiate cancers or tumors without irradiating non-cancerous tissue or reducing the amount of radiation hitting non-cancerous tissue.

It is an object of this invention to inhibit electrons from scattering or diverging during radiation treatment of a patient. It is a further object to cause electrons to travel in a helical trajectory. It is another object to use magnets to induce the helical path of electrons.

It is an object of this invention to treat cancer patients, human or animal, with radiation in the form of electrons having a helical trajectory. It is an object of this invention to treat various cancers such as, but not limited to, breast cancer, melanoma, head and neck cancer, lymphomas, nasopharyngeal carcinoma, sarcomas in the extremities, and testicular cancer.

It is an object of this invention to conduct radiation therapy in patients having cancer wherein the radiation therapy uses a helical electron beam. It is a further object of this invention to treat cancer with a helical electron beam while avoiding unnecessary irradiation of the patient's non-cancerous tissue.

It is an object of this invention to have a device that emits a helical electron beam for conducting radiation therapy for cancer in patients. It is a further object that this device will assist in avoiding unnecessary irradiation of the patient's normal tissue.

It is another object of this invention to treat a patient with breast cancer and in need of treatment with a helical electron beam with a conformal dose distribution that is targeted to the whole breast, the chest wall, and/or the internal mammary nodes. It is a further object to prevent excessive irradiation of the heart and/or lung.

It is an object of this invention to have a device for generating helical electron beams with a conformal dose distribution for radiation therapy in order to treat whole breast, the chest wall, and/or the internal mammary nodes. It is a further object to this invention that this device will assist in preventing excessive irradiation of the heart and/or lung.

It is an object of this invention to have a device that when used in conjunction with a linear accelerator that the combination emits a helical electron beam. It is a further object of this invention that the electron beam is collimated at or near the patient's skin surface. It is a further object of this invention that the electron beam is collimated between 0 cm to 40 cm from the patient's skin and most preferably between 0 cm and 10 cm from the patient's skin.

It is an object of this invention to have a device that when used in conjunction with a linear accelerator that the combination emits a helical electron beam. It is a further object of this invention that the device reduces the electron beam's divergence and penumbra. It is a further object of this invention that the shape of the field of the helical electron beam ranges between 0.01 cm$^2$ to 800 cm$^2$, and more preferably between 0.5 cm$^2$ and 10 cm$^2$.

It is an object of this invention to have a device for generating helical electron beams for radiation therapy whereby the field size of the treatment area is between 0.1 cm$^2$ and 200 cm$^2$ and more preferably between 0.2 cm$^2$ and 1.0 cm$^2$.

It is an object of this invention that the energy of the foil modulate the energy of the electrons passing through the foil. It is a further object of this invention that the modulated electrons have energy ranging between 0.5 MeV and 40 MeV and more preferably between 4 MeV and 20 MeV.

It is an object of this invention to have a device for generating a helical electron beam wherein the device uses a linear accelerator to generate the electron beam and a magnet with the magnetic field in a parallel path as the direction of travel of the electrons. It is a further object of this invention to use at least one foil to modulate the energy of the electrons.

It is an object of this invention to have a device for generating a helical electron beam wherein the device uses a linear accelerator to generate the electron beam and a magnet with the magnetic field in a parallel path as the direction of travel of the electrons. It is a further object of this invention to use at least one foil to modulate the energy of the electrons. It is a further object of this invention to have a multileaf collimator adjacent to or within close proximity to the magnet. It is a further object of this invention to be able to move the magnet and the multileaf collimator quickly and easily into proper position for treatment.

Figure 6A:
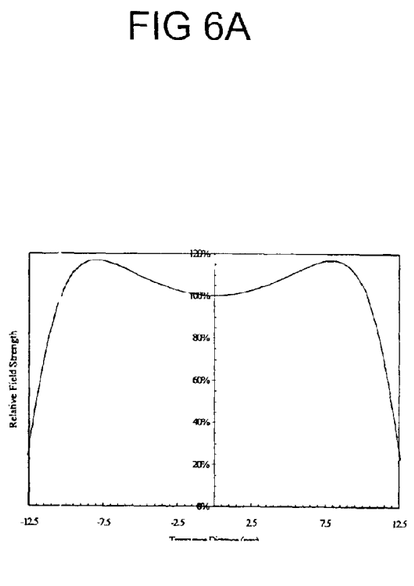
FIGS. 6A–6B illustrate the magnetic field profiles of a collimator according to an embodiment of the invention.
Figure 6B:
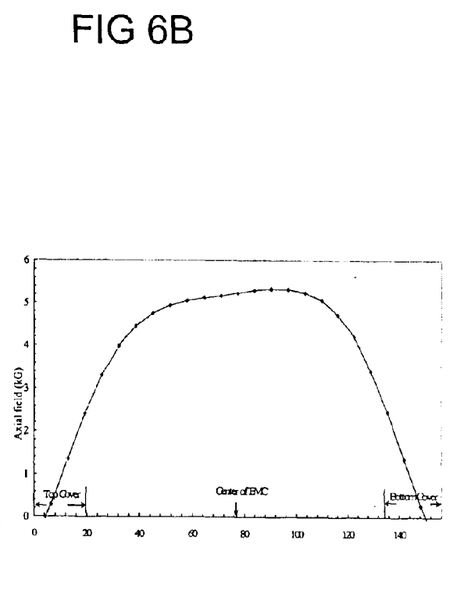

FIGS. 6A-B illustrate the magnetic field profiles of a collimator according to an embodiment of the invention.

DETAILED DESCRIPTION OF THE INVENTION

Static magnetic fields can shape the electron paths. Under an axial magnetic field, any scatter or divergent electrons can be constrained to follow helical trajectories. The simulation of electron beam trajectories under an axial magnetic field indicates electrons traveling in a helical path. Electrons under an axial magnetic field have a much sharper penumbra and improved range straggling. However, strong magnetic fields about 3–6 Telsa are needed to generate a useful helical electron beam with gyration radius of 1–2 mm [59]. Such strong magnetic fields require bulky and expensive superconducting magnets.

Figure 1:
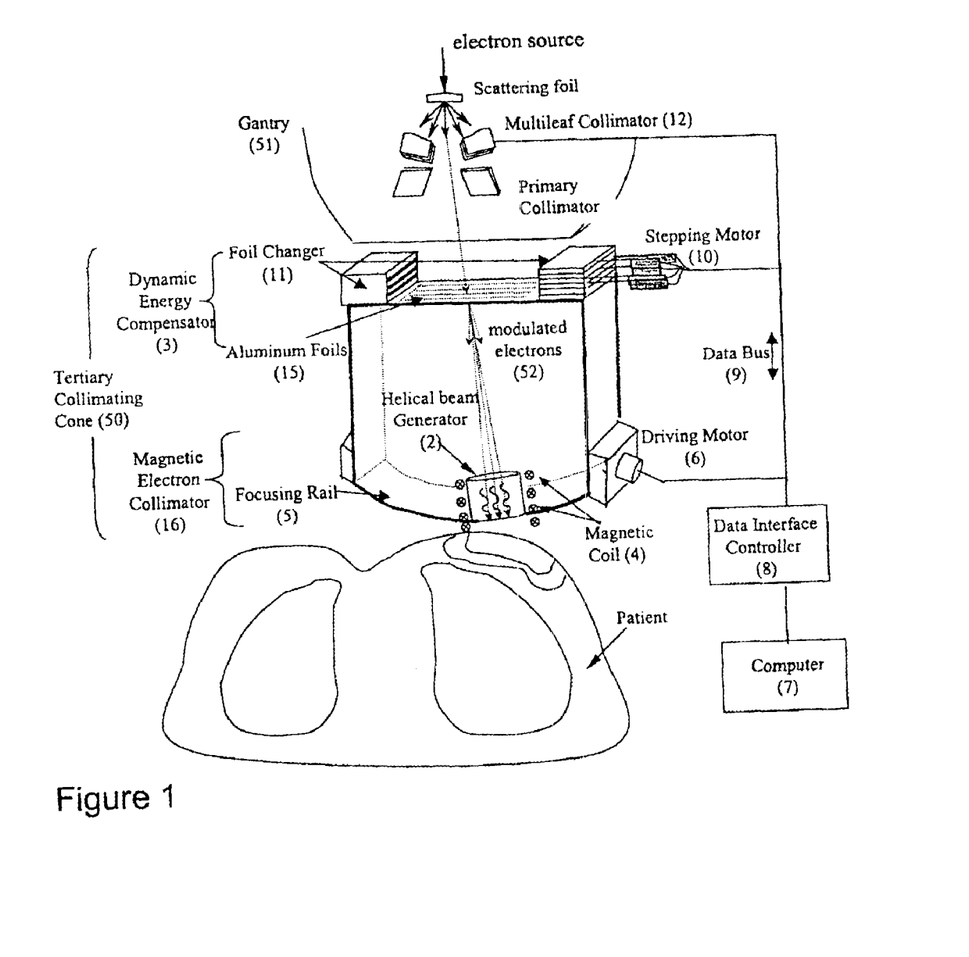
FIG. 1 is a perspective view of the tertiary collimating system for generating helical electron beams according to a first embodiment.

As shown in FIG. 1, the preferred embodiment of this invention uses a tertiary collimating cone, 50, having a magnetic electron collimator, 16, and a dynamic energy compensator, 3, to generate a modulated electron beam that travels in a helical path. The magnetic electron collimator contains a helical beam generator, 2, which uses a magnetic coil, 4, that produces a magnetic field direction that is aligned with the direction of movement of the electron beam. As a result, the solid angle of each individual modulated electron field is significantly reduced. This arrangement effectively decreases the axial magnetic field required for producing desired helical electron beams.

When electrons pass through a magnetic field, they are confined to travel in helical trajectories about an axis parallel to the magnetic field lines with a specific gyration radius. The gyration radius is determined by the following formula:

$$a = \frac{p\perp}{3 \times 10^{-7} B} \quad \text{(Formula 1)}$$

where $\alpha$ is the gyration radius in cm, $p\perp$ is the momentum perpendicular to the magnetic field lines in MeV/c (c is the speed of light in vacuum), and B is the magnetic field strength in kilo-gauss (kG). Because of this confinement, the resulting fluence at the phantom or patient plane will be increased resulting in dose distributions that will potentially improve the treatments of various cancers such as, but not limited to, breast cancer, melanoma, head and neck cancer, lymphomas, nasopharyngeal carcinoma, sarcomas in the extremities, and testicular cancer.

For example, if a patient is treated at 100 cm Source to Skin Distance (SSD) by superposing modulated electron fields up to 3×3 cm², then only magnetic field of 3–5 kG instead of 3–5 Tesla is needed to produce helical electron beams with gyration radius of 1–2 mm. Such uniform magnetic fields are generated using regular Helmhotz magnetic coils, but any hollow-shape magnets can work. A magentized material such as Nb-35 is an example of an alternative magnet. Because the needed field strength is dependent on the scanning field size and initial beam energy, magnetic fields can range from 0.5 kG to 50 kG. For specific beast cancer or chest wall treatments, helical electron beams ranging from 10 MeV to 20 MeV use magnetic field modulations ranging from 1 kG to 100 kG. For superficial cancer such as melanoma, helical electron beams range from 0.5 MeV to 8 MeV use magnetic field strengths ranging from 0.5 kG to 100 kG. For head and neck cancers involving lymph nodes such as nasopharyngeal carcinoma, helical electron beams ranging from 5 MeV to 15 MeV use magnetic field strengths ranging from 10 kG to 200 kG. For other cancers such as soft-tissue sarcoma in extremities, it is preferable to use finely adjusted helical electron beams ranging from 4 MeV to 20 MeV with magnetic field strengths ranging from 0.5 kG to 200 kG.

As shown in FIG. 1, in the preferred embodiment, this invention is a tertiary collimating cone, 50, which is mounted to the gantry, 51, of a typical linear accelerator at the gantry's attachment ports. The linear accelerator contains various components that are well known in the art field. In summary, the linear accelerator contains an electron source, 53, which produces an electron beam, 54. The electron beam passes through a scattering foil, 55, and may pass through a primary collimator, 56, and a multileaf collimator, 12, prior to exiting the gantry. It is known in the art field that the position of and order of passage through the multileaf collimator and the primary collimator can vary within the gantry.

In an alternative embodiment, the tertiary collimating cone, 50, can be attached to a movable stand, instead of attaching the tertiary collimating cone to the gantry of the linear accelerator. In this manner, one can move the tertiary collimating cone in the correct position between the patient and the linear accelerator. Then one can detachably secure the stand and tertiary collimating cone to the floor, wall, ceiling, table, gantry, or other site, so that the tertiary collimating cone does not move during treatment.

Alternatively, various components of the tertiary collimating cone can be added to the inside of the gantry. In this alternative embodiment, the magnetic electron collimator, 16, and dynamic energy compensator, 3, can be placed inside the gantry. Alternatively, the helical beam generator, 2, can be placed inside the gantry in line with the path of the electrons that pass through the primary collimator and the multileaf collimator. Foils or other forms for modulating electron energy can be placed between the collimators and the helical beam generator.

As shown in FIG. 1, in the preferred embodiment, the tertiary collimating cone, 50, contains a dynamic energy compensator, 3, and a magnetic electron collimator, 16. The dynamic energy compensator, 3, contains two foil changers, 11, foils, 15, and a stepping motor, 10. The foil changers are located across from each other at the entrance of the tertiary collimating cone. The foils, 15, are held by and stored within the foil changers, 11. While it is preferable to have at least fifteen foils in the dynamic energy compensator, more or less foils can be used. It is even possible to not have any foils, if the energy of the electrons is appropriate. The actual number of foils used can vary based on the energy of the electron beam and the desired final energy of the helical electron beam. The foils can range in thickness between 0.5 mm to 5 mm, and most preferably range in thickness between 1 mm to 2 mm. The foils can be made from aluminum, tungsten, tantalum, titanium, beryllium, copper, lead, any medium atomic number metals, and/or alloys of any medium atomic number metals. The stepping motor, 10, moves each foil independently of each other. The foils block the electron beam, 54, dynamically during a treatment to produce modulated electrons, 52. One problem that may occur is that the electrons can strike the foil and create X-rays. This potential production of X-rays can be reduced to an insignificant amount by using mesh type foils and/or having the foils made from different metals or alloys. Foil thickness can also help alleviate the potential production of X-rays.

Modulated electrons have different properties than the electron beam, 54, emitted from the electron source, 53. The electron beam loses about 100–800 keV after penetrating one sheet of foil. The dynamic energy compensator, 3, effectively produces modulated electron beams that can range between 0.5 MeV and 40 MeV, but most preferably varying from 4 MeV to 20 MeV.

The magnetic electron collimator, 16, is located downstream from the dynamic energy compensator, 3, in the tertiary collimating cone, 50. The magnetic electron collimator has a dynamically focused helical beam generator, 2. The helical beam generator is a magnetic coil, 4, which produces an axial magnetic field, relative to the path of the modulated electrons.

In the preferred embodiment, the magnetic coil, 4, contained within the helical beam generator, 2, produces axial magnetic field ranging from 0.5 kG to 200 kG, depending on the type of cancer or tumor being treated. The inner diameter of the magnetic coil in the helical beam generator can vary. The preferred inner diameter opening is between 0.1 cm and 30 cm, and most preferably between 1 cm and 20 cm.

In the preferred embodiment, the tertiary collimating cone has a locator controller which controls the location of the helical beam generator. In the preferred embodiment, the helical beam generator is attached to a focusing rail, 5. A driving motor, 6, is attached to and moves the focusing rail. As the focusing rail moves, the helical beam generator also moves. The driving motor is located on the exterior of the tertiary collimating cone and uses a stepping motor to move the focusing rail. The driving motor moves the focusing rail, and thus the helical beam generator into the desired position for optimal focusing of the electrons on the area of treatment. The helical beam generator can be located at any position along the bottom surface of the tertiary collimating cone. The helical beam generator can rotate 180°; the axis of rotation being perpendicular to the plane of the patient's skin in the area of treatment. A computer, 7, controls the driving motor and thus the movement of the helical beam generator along the focusing rail. The computer contains software that uses predetermined algorithms to determine the optimum position of the helical beam generator, the optimum dosage, and the optimum treatment protocol. This arrangement permits quick repositioning of the helical beam generator during radiation therapy sessions, thereby permitting small fields of treatment and treatment of many fields in one radiation therapy session. The radiation field size can range between 0.1 cm$^2$ and 200 cm$^2$, and most preferably between 0.2 cm$^2$ and 1.0 cm$^2$. The speed of the computer, the algorithm, and the precision of the stepping motor all play a role in determining the size of the radiation field.

Figure 2:
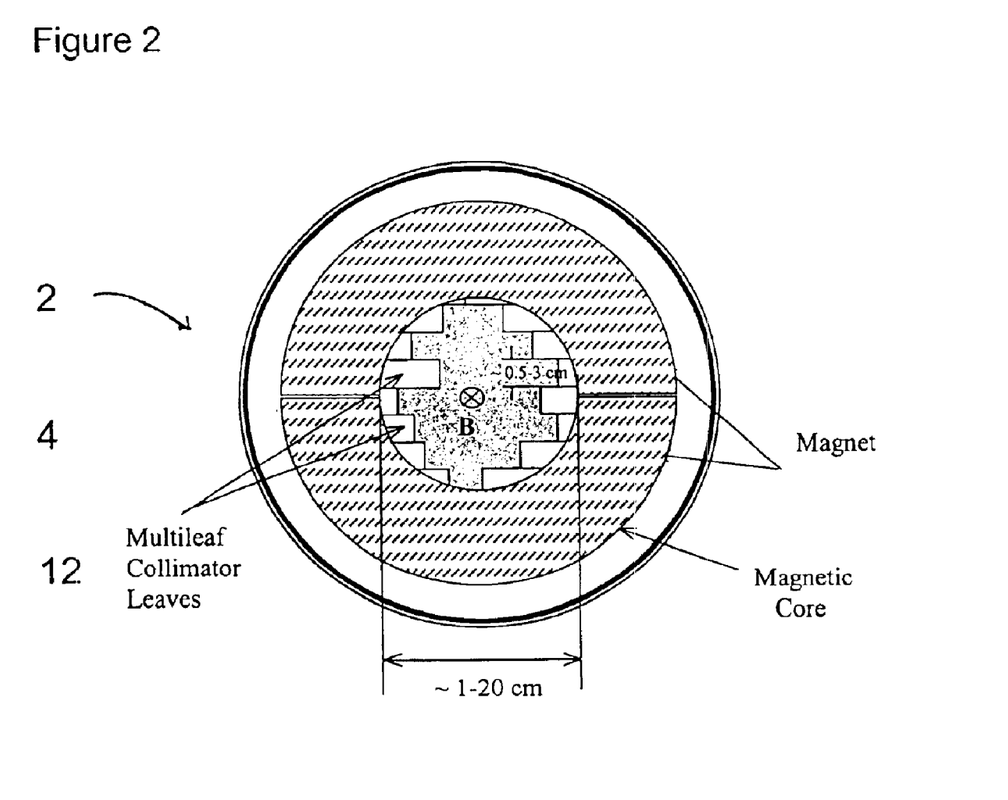
FIG. 2 is a cross sectional view an alternative embodiment of the helical beam generator.

In an alternative embodiment of this invention as illustrated in FIG. 2, a multileaf collimator, 12, is present within the magnetic electron collimator, 16. While FIG. 2 illustrates a multileaf collimator upstream of the magnetic coil, 4, the multileaf collimator can also be located downstream, or both upstream and downstream of the magnetic coil. Any of the various well known in the art field types of multileaf collimators can be used. In this alternative embodiment, the linear accelerator can either have a multileaf collimator or lack a multileaf collimator. Because electrons are being modulated rather than photons, the multileaf collimator within the magnetic electron collimator, 16, required a much smaller leaf thickness than is required for other types of particles. In this alternative embodiment, the leaves of the multileaf collimator can range in thickness between 0.3 cm to 5 cm, and most preferably between 0.5 cm and 3.0 cm. This reduction in thickness in the multileaf collimator within the magnetic electron collimator significantly reduces the overall weight of the tertiary collimating cone, 50. Placing a multileaf collimator within the tertiary collimating cone provides for better focusing of the electron beam on the tumor and enables one to prevent applying the helical electron beam onto normal tissue. In this alternative embodiment, the multileaf collimator within the magnetic collimating cone also plays a role in determining the size of the radiation field.

The helical electron beam exits the helical beam generator located along the bottom surface of the tertiary collimating cone prior to striking the patient. The distance from the bottom surface of the tertiary collimating cone to the patient's skin can range from 0 cm to +40 cm, and most preferably from 0 cm to 10 cm. It is possible that part of the patient can enter inside the helical beam generator in which case that area of the patient is located a negative distance from the bottom surface of the tertiary collimating cone.

Because this invention collimates the electron beam at or near the patient's skin surface, the invention reduces the electron beam's divergence and penumbra.

A computer, 7, assists in determining the optimal position, moving the helical beam generator to the optimal position, and verifying that the helical beam generator is in the correct optimal position. The computer receives information from and transmits information to the helical beam generator via a data interface controller, 8, and a data bus, 9. The data interface controller and data bus also relay information from the computer to the stepping motor, 10, which controls the movement of the foil changer, 11, and back to the computer. The data interface controller and data bus also relay information from the computer to the multileaf collimator, 12, and back to the computer. The computer also assists in determining the optimal field size for the radiation treatment. If a multileaf collimator is located inside the tertiary collimating cone, 50, that multileaf collimator is also under the control of the computer, 7.

An algorithm, similar to photon IMRT beam delivery algorithms, is stored within the computer, 7. The algorithm assists in determining the correct position of the helical beam generator, 2, and the dynamic energy compensator, 3. The algorithms are based on the criteria of minimum total beam-delivery time and maximum dose accuracy. The algorithm uses a user-developed treatment planning system with graphical user interface.

The computer also contains an interface for quality assurance. For each patient, a graphical time-dose sequence based on patient CT data and the beam delivery sequence control data is produced to display the accumulated dose delivered to the patient. This procedure allows accurate verification of the time-dose relationship. If any interruption happens during the treatment, the actual delivered dose is recovered from the actual beam-on time. Any leftover sequence is then compensated accurately once the interruption is cleared.

Software is used to simulate the time-dose sequence based on patient CT data and treatment plan generated from HEART (Helical Electron Avoidance Radiation Therapy) delivery control files. For each patient, the time-dose sequence for the entire delivery is simulated using computer software for pretreatment quality assurance of a treatment delivery. Therefore, any interruption during the treatment delivery allows the operator to recover the interruption based on the simulated sequence to within 2% of the desired dose.

In the preferred embodiment of this invention, one plans radiation dose coverage of a given target volume by first segmenting the entire depth of the target into approximately fifteen discrete distances, each corresponding to one or more levels of modulated beam energies. The shape of the target in electron beam's eye view for each distance is back-projected to determine the port of an intensity modulated electron beam for the select beam energy. The computer, using an algorithm based on the measured data table such as percentage depth dose (PDD), determines the beam intensity profile to cover the target at the desired depth. A standard least-square minimization method such as conjugate gradient search is used to optimize the weights of the intensity-modulated beams to achieve uniform and conformal dose coverage to the target.

While this embodiment for radiation dose coverage is preferred, other beam optimization algorithms which are well known in the art field, such as simulated annealing, linear and non-linear programming techniques can be used.

The overall size and shape of the tertiary collimating cone can vary. It may be preferable that its height range between 20 cm to 80 cm and that it measures between 20 cm to 80 cm from side to side.

FIGS. 6A and 6B illustrate magnetic field profiles of a prototype electron magnetic collimator. FIG. 6A is the normalized transverse magnetic field and FIG. 6B is the axial magnetic profile along the central axis. The fringe field was minimized through an aluminum and delrin shield of the collimator. The field was formed using a cylindrical shape collimator with an outside diameter of 12 cm, an inside diameter of 3 cm and a length of about 12–13 cm. The longer the length of the magnetic collimator, the lower the magnetic field required.

For radiation cancer therapy, this invention permits greater accuracy and efficiency in doses, ranges of doses, depth of treatments, duration of treatments, and number of fractions. This invention also permits better targeting of radiation and highly reduces the amount of scattering of radiation outside the tumor tissue into normal tissue. This invention permits one to have more conformal treatment of tumor while sparing normal tissue from the radiation.

A Monte Carlo study was performed using a preferred embodiment of this invention. In this study, 15 MeV electrons were generated by an EGS4/BEAM simulation of an Elekta SL20 linear accelerator with the standard, known in the art field 10×10 cm$^2$ electron cone (Elekta Oncology Systems Ltd., West Sussex, UK) attached to the end of the linear accelerator gantry. A version of the EGS4/DOSXYZ code was modified to generate the magnetic field module developed by Nelson and Rogers et al. [67–68]. In the simulation, a magnetic field with field lines parallel to the beam direction was applied in the region of air extending 10 cm immediately beyond the standard electron cone. (It is to be understood that in the invention, the magnetic field will be generated inside the tertiary collimating cone and can extend beyond the end of the tertiary collimating cone.) In the simulation, the magnetic field strengths used varied from 0 kG to 50 kG. A 100-cm$^3$ water phantom for scoring dose was placed at the end of the 10-cm region.

With no magnetic field (0 kG) the electrons diverge to more than −7.5 cm and +7.5 cm from the center of the travel path as they travel further away from the end of the electron cone resulting in a broader field at the phantom surface. With magnetic fields of 10 kG and 50 kG the electrons are forced to move in a "tunnel" with dimensions defined by the 10×10 cm$^2$ aperture of the electron cone. In the 10 kG magnetic field, the electrons diverged approximately −6.25 cm and +6.25 cm from the center of the travel path. In the 50 kG magnetic field, the electrons barely diverged out of the tunnel of the 10×10 cm$^2$ path defined by the electron cone. Using a 10 kG or 50 kG magnetic field, a more constrained dose distribution is achieved in the water phantom.

The isodose contours in the xz plane of the water phantom with no magnetic field (0 kG) and for a magnetic field of 10 kG and 50 kG indicate that with increasing magnetic field strength, the distribution of the electrons becomes more compact. The penumbra region decreased between approximately 10% to 50%, depending on the field strength. The higher the magnetic field, the smaller becomes the penumbra. The penumbra is defined as between 20% to 80% of the dose profile.

Figure 3:
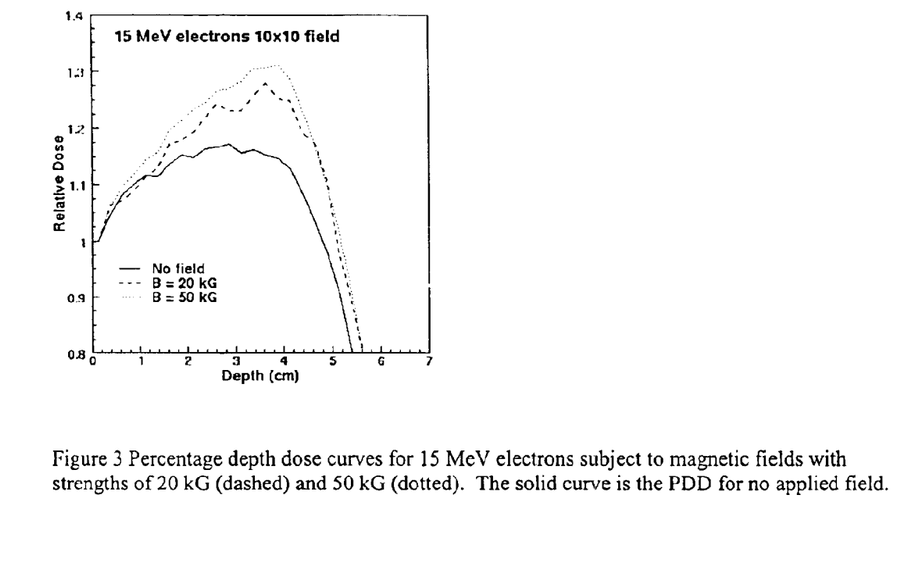
FIG. 3 illustrates the relative dose of the electrons at zero magnetic field, 20 kG magnetic field, and 50 kG magnetic field.

Another effect of the magnetic field is the enhancement of the dose distribution as a function of depth within the water phantom. FIG. 3 shows the central-axis depth dose curves for three cases (no field (—), B=20 kG ( - - - ), and B=50 kG ( . . . )). The curves are all normalized to the dose at the surface. In FIG. 3, with no magnetic field (—), the dose distribution reaches a maximum of 1.15 at a depth of 2.5 cm. In a 20 kG magnetic field ( - - - ), the dose distribution is enhanced to a maximum of 1.25 at a depth of 4 cm. With a 50 kG magnetic field ( . . . ), the dose distribution is enhanced further to a maximum of 1.32 at a depth of 4.2 cm.

Figure 4:
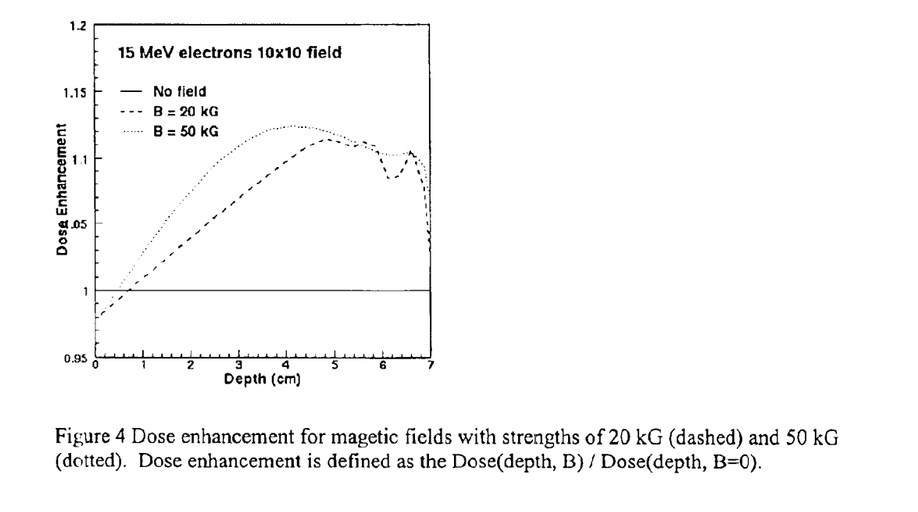
FIG. 4 illustrates the dose enhancement of the electrons at various depths for zero magnetic field, 20 kG magnetic field, and 50 kG magnetic field.

The dose enhancement E is defined according to the following formula:

$$E(d, B) = \frac{D(d, b)}{D(d, B = 0)} \quad \text{(Formula 2)}$$

where D(d,B) is the dose at depth d with a magnetic field strength B applied to the 10-cm region in air just beyond the cone. FIG. 4 shows E as a function of d for B=20 kG ( - - - ) and B=50 kG ( . . . ), as compared to no magnetic field (—). With a magnetic field of 50 kG, the maximum dose enhancement occurs between 3–4 cm, declines slightly from 4 cm up to 7 cm and then approaches zero at approximately 7 cm. With a magnetic field of 20 kG, the maximum dose enhancement occurs between 4.5 cm and 5.7 cm and is equal in dose enhancement to the dose enhancement in the 50 kG magnetic field. The dose enhancement drops and regains strength in the 20 kG magnetic field between 5.8 cm and 6.5 cm then approaches zero at approximately 7 cm.

Figure 5:
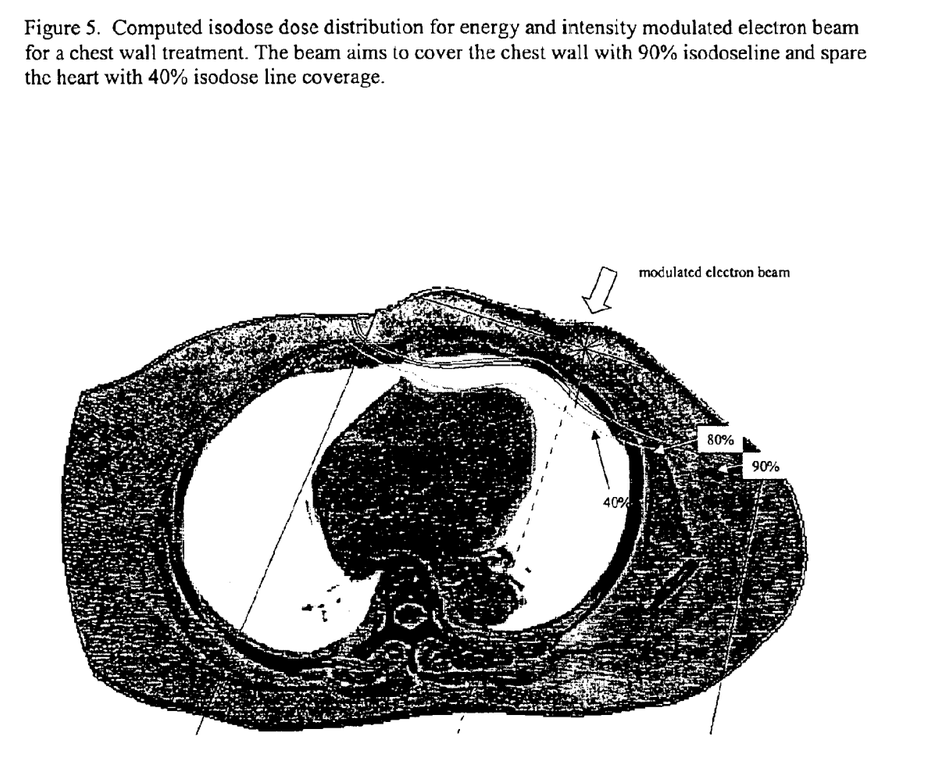
FIG. 5 illustrates the computed isodose dose distribution of an energy and intensity modulated electron beam for a chest wall treatment.

FIG. 5 illustrates a study of modulated helical electron beam influence distribution for chest wall treatment that was performed using analytical pencil-beam models [64–65]. The helical electron beam energy modulation was generated by superposing several helical electron beams of different energies and weights. The chest wall was treated with at least 90% isodose while the heart received less than 40% isodose. The part of the lung in the region that is closest to the device receives approximately 80% isodose. But the isodose quickly drops to less than 40% as one gets closer to the heart. Thus, usage of this device to treat cancers located on the chest results in lower amount of radiation irradiating the heart and lungs as compared to regular electron beam radiation and compared to other forms of radiation treatment. Helical electron beams increase the avoidance of radiating healthy tissue during radiation treatment of cancers. The device helps prevent radiation injury of healthy tissue during radiation therapy of cancers by three different approaches. The first approach is by enhancing the dose of the radiation to a smaller area. The second approach is by lowering the depth and spread of the radiation. And third by allowing one to use smaller areas of treatment than is permitted using standard, known in the art field linear accelerators with a multileaf collimator in the gantry.

A Monte Carlo method to determine how dose enhancements can be improved by using a helical electron beam was undertaken.

To further quantify the dose enhancement, we define a ratio $R_{pdd}$, $$R_{pdd} = \frac{D(x = x_{ref})}{D(x = x_{surf})}, \quad (3)$$

where $D(x)$ is a dose along the central axis at a depth x, $x_{ref}$ is a reference depth, and $x_{surf}$ is a depth near the surface. For our study, we took $x_{surf}$ to be 0.25 cm. For most of the distributions the maximum was close to 4.5 cm, so we set $x_{ref}$ to this value.

In order to better understand the effect, we studied $R_{pdd}$ as a function of $N_{rot}$, where $N_{rot}$ is the number of rotations the electron undergoes while in the magnetic field and is given by $$N_{rot} = \frac{\omega_g t}{2\pi}, \quad (4)$$

where $\omega_g$ is the frequency with which electrons orbit in a magnetic field is given by $$\omega_g = \frac{1}{\gamma}\omega^e_{cycl}|B|, \quad (4')$$

where $\gamma=1+T/(mc^2)$ is the Lorentz relativistic boost factor (T and m are the kinetic energy and rest mass of the particle, respectively), and $\omega^e_{cycl}$ is the electron cyclotron frequency which is a constant of nature and is approximately $\omega^e_{cycl} \approx 1.758\ 82 \times 10^{11}$ rad s$^{-1}$T$^{-1}$ and t is the amount of time the electron spends in the field. This can be written as $$t = \frac{d}{\beta_\parallel v}, \quad (5)$$

where $\beta_\parallel$ is the electron's component parallel to the beam axis relative to its absolute velocity, and $v$ is the absolute velocity of the electron, and d is the distance traversed by the electron. Since the electrons are highly relativistic, v can be taken to be the speed of light in a vacuum c. The relativistic expression $\beta = p/E$ can then be used to write $\beta_\parallel$ as $$\beta_\parallel = \frac{p_\parallel c}{E}, \quad (6)$$

where $p_\parallel$ is the electron's component of momentum parallel to the beam axis. This can be written as $$p_\parallel = |p|\cos\theta, \quad (7)$$

where $\theta$ is the angle the momentum vector makes with the central axis. Combining Eq. (4'), (4)–(6), and (7) we arrive at an expression for $N_{rot}$, $$N_{rot} = \frac{1}{2\pi}\frac{|B|d(T+mc^2)}{\gamma|p|c^2\cos\theta}\omega^e_{cycl}. \quad (8)$$

By making the following approximations:

$$T+mc^2 \approx |p|c, \quad (9)$$

$$\cos\theta \approx 1, \quad (10)$$

the expression for $N_{rot}$ is reduced to $$N_{rot} \approx \frac{1}{2\pi\gamma c}|B|d\,\omega^e_{cycl}. \quad (11)$$

Figure 7:
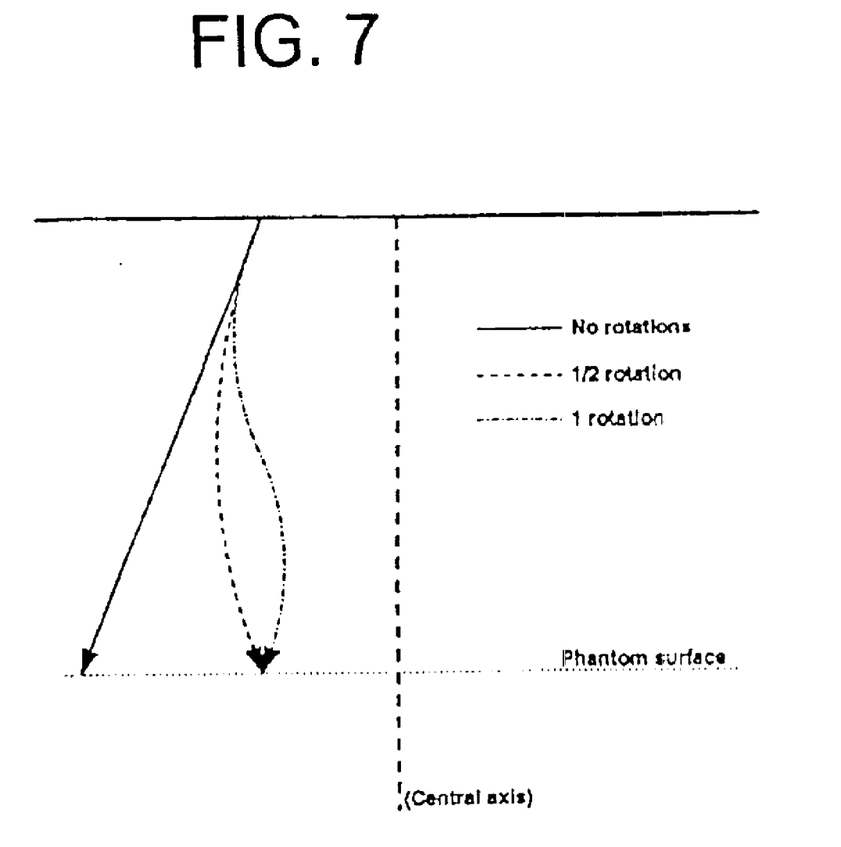
FIG. 7 illustrates electrons undergoing rotation along a helical path in conjunction with application of a magnetic field.

The maximum enhancement occurs when the electrons undergo $$n + \frac{1}{2}$$

rotations (n is an integer) while enhancement is minimized when they undergo full rotations. FIG. 7 illustrates the focusing effect with the application of a magnetic field. With a magnetic field applied so that an electron undergoes a full rotation, electrons are directed away from a central axis. With a magnetic field applied so that electrons undergo a half rotation, electrons are directed toward the central axis.

All references cited herein are incorporated by reference in their entirety.

1. Lichter A S, Lippman M E, Danforth D N Jr, d'Angelo T, Steinberg S M, deMoss E, MacDonald H D, Reichert C M, Merino M, Swain S M, et al. Mastectomy versus breast-conserving therapy in the treatment of stage I and II carcinoma of the breast: a randomized trial at the National Cancer Institute. *J Clin Oncol*. 10(6): 976–83, 1992.
2. Host H, Brennhovd I O, Loeb M. Postoperative radiotherapy in breast cancer: long-term results from the Oslo Study. *Int J of Radiat. Oncol Biol Phys*. 12:727–732, 1986.
3. Fisher B, Anderson S, Redmond C K, et al. Reanalysis and results after 12 years of follow-up in a randomized clinical trial comparing total mastectomy with lumpectomy with or without irradiation in the treatment of breast cancer. *New England J of Med*. 333(22): 1456–1461, 1995.
4. Blichert-Toft M, Rose C, Andersen J A, et al. Danish randomized trial comparing breast conservation therapy with mastectomy: six years of life-table analysis. *J National Cancer Inst*. 11: 19–25, 1992.
5. Early Breast Cancer Trialists' Collaborative Group. Effects of radiotherapy and surgery in early breast cancer. *N Eng J Med*. 333: 1444–55, 1995.
6. The Steering Committee on Clinical Practice Guidelines for the Care and Treatment of Breast Cancer. Mastectomy or lumpectomy? The choice of operation for clinical stage I and II breast cancer. CMAJ 158. Suppl. 3: S15–21.
7. Van Dongen J A, Bartelink H, Fentiman I S, et al. Randomized clinical trial to assess the value of breast-conserving therapy in stage I and II breast cancer, EORTC 10801 trial. *J National Cancer Inst*. 11: 15–18, 1992.
8. Sarrazin D, Le M G, Arriagada R, et al. Ten-year results of a randomized trial comparing a conservative treatment to mastectomy in early breast cancer. *Radiother and Oncol*. 14(3): 177–184, 1989.
9. Jacobson J A, Danforth D N, Cowan K H, et al. Ten-year results of a comparison of conservation with mastectomy in the treatment of stage I and II breast cancer. *New England J of Med*. 332(14): 907–911, 1995.
10. Sheldon T, Hayes D F, Cady B, Parker L, Osteen R, Silver B, Recht A, Come S, Henderson I C, Harris J R. Primary radiation therapy for locally advanced breast cancer. *Cancer*. 60(6): 1219–25, 1987.
11. Schwaibold F, Fowble B L, Solin L J, Schultz D J, Goodman R L. The results of radiation therapy for isolated local regional recurrence after mastectomy. *Int J Radiat Oncol Biol Phys* 21(2): 299–310, 1991.
12. Pierce L J, Glatstein E Cancer. Postmastectomy radiotherapy in the management of operable breast cancer. 74: 477–485, 1994.
13. Cheng S H, Jian J J, Chan K Y, Tsai S Y, Liu M C, Chen C M. The benefit and risk of postmastectomy radiation therapy in patients with high-risk breast cancers. *Am J Clin Oncol* 21(1): 12–7, 1998.
14. Weshler Z, Brufman G, Sulkes A, Warner-Efraty E, Ben-Baruch N, Biran S, Fuks Z. Radiation therapy for locally advanced breast cancer: prognostic factors and complication rate. *Eur J Surg Oncol* 6(5): 430–435, 1991.
15. Metz J M, Schultz D J, Fox K, Glick J, Solin L J. Long-term outcome after postmastectomy radiation therapy for breast cancer patients at high risk for local-regional recurrence. *Cancer J Sci Am.* 5(2): 77–83, 1999.
16. Hsi R A, Antell A, Schultz D J, Solin L J. Radiation therapy for chest wall recurrence of breast cancer after mastectomy in a favorable subgroup of patients. *Int J Radiat Oncol Biol Phys* 42(3): 495–499, 1998.
17. Groth S, Zaric A, Sorensen P B et al. Regional lung function impairment following post-operative radiotherapy for breast cancer using direct or tangential field techniques. *Br J Radiol* 59: 445–451, 1986.
18. Haybittle J L, Brinkley D, Houghton J, et al. Postoperative radiotherapy and late mortality: evidence from the Cancer Research Campaign trial for early breast cancer. *British J Med.* 298:1611–1624, 1989.
19. Inskip P D, Stovall M, Flannery J T. Lung cancer risk and radiation dose among women treated for breast cancer. *J National Cancer Inst.* 86(13): 983–8, 1994.
20. Gyenes G, Fomander T, Carlens P, Glas U, Rutqvist L E. Myocardial damage in breast cancer patients treated with adjuvant radiotherapy: a prospective study. *Int J Radiat Oncol Biol Phys.* 36(4): 899–905, 1996.
21. Dodwell D J, Langlands A: Cardiac morbidity of post-operative adjuvant radiotherapy for breast cancer, A review. *Austral sian Radiol* 38: 154–156, 1994.
22. Rutqvist L E, Liedberg A, Hammar N, Dalberg K. Myocardial infarction among women with early-stage breast cancer treated with conservative surgery and breast irradiation. *Int J Radiat Oncol Biol Phys.* 40(2): 359–63, 1998.
23. Gyenes G, Gagliardi G, Lax I, Fornander T, Rutqvist L E. Evaluation of irradiated heart volumes in stage I breast cancer patients treated with postoperative adjuvant radiother. *J Clin Oncol* 15(4): 1348–53, 1998.
24. Gyenes G. Radiation-induced ischemic heart disease in breast cancer—a review. *Acta Oncol.* 37(3): 241–6, 1998.
25. Gyenes G, Rutqvist L E, Liedberg A, Fornander T. Long-term cardiac morbidity and mortality in a randomized trial of pre- and postoperative radiation therapy versus surgery alone in primary breast cancer. *Radiother Oncol* 48(2): 185–190, 1998.
26. Paszat L F, Mackillop W J, Groome P A, Schulze K, Holowaty E. Mortality from myocardial infarction following postlumpectomy radiotherapy for breast cancer: a population-based study in Ontario, Canada. *Int J Radiat Oncol Biol Phys.* 43(4):755–762 1999.
27. Gonzaga A T, Antunes M J. Post-radiation valvular and coronary artery disease. *J Heart Valve Dis.* 6(2): 219–21, 1997.
28. Meeks S L, Buatti J M, Bova F J, Friedman W A, Mendenhall W M, Zlotecki R A. Potential clinical efficacy of intensity-modulated conformal therapy. *Int J Radiat Oncol Biol Phys* 40(2): 483–95, 1998.
29. Samson M J, van Sornsen de Koste J R, de Boer H C, Tankink H, Verstraate M, Essers M, Visser A G, Senan S. An analysis of anatomic landmark mobility and setup deviations in radiotherapy for lung cancer. *Int J Radiat Oncol Biol Phys* 43(4): 827–32, 1999.
30. Brame A. Optimization of radiation therapy and the development of multileaf collimation. *Int J Radiat Oncol Biol Phys.* 25:373–375, 1993.
31. Kallman P, Lind B, Eklof A, Brahme A. Shaping of arbitrary dose distributions by dynamic multileaf collimators. *Phys Med Biol.* 33: 1291–1300, 1988.
32. Convery D J, Rosenbloom M E. The generation of intensity-modulated fields for conformal radiotherapy by dynamic multileaf collimators. *Phys. Med. Biol.* 37
33. Xing L, Hamilton R J, Spelbring D, Pelizzari C A, Chen, G T Y, Boyer, A L. Fast iterative algorithms for three-dimensional inverse treatment planning. *Med Phys.* 25:1845–1849, 1998.
34. Webb S. Optimizing the planning of intensity-modulated radiotherapy. *Phys Med Biol.*, 39:2229–2246, 1994.
35. Carol M. An automatic 3-D treatment planning and implementation system for optimized conformal therapy by the Nomos Corporation. *Int J Radiat Oncol Biol Phys.* 23:1081, 1992.
36. Galvin J M, Chen X, Smith R M. Combining multileaf fields to modulate fluence distributions. *Int. J. Radiat. Oncol. Biol. Phys*, 27: 697–705, 1993.
37. Bortfeld T, Boyer A L, Schlegel W, Kahler D L, Waldron T J. Realization and verification of three-dimensional conformation radiotherapy with modulated fields. *Int J Radiat Oncol Biol Phys.* 30: 899–908, 1994.
38. Fraass B A, McShan D L, Kessler M L, Matrone G M, Lewis J D, Weaver T A. A computer-controlled conformal radiotherapy system I: overview. *Int. J. Radiat. Oncol. Biol. Phys.* 33:1139–1157, 1995.
39. Mackie T R, Holmes T W, Swerdloff S, Reckwerdt P J, Deasy J O, Yang J, Paliwal B R, Kinsella T J. Tomotherapy: A new concept for the delivery of conformal therapy using dynamic compensation, *Med Phys.* 20: 1709–1719, 1993.
40. Holmes T W, Mackie T R. A comparison of three inverse treatment planning algorithms. *Phys Med Biol.* 39:91–106, 1994.
41. Yu, C X. Intensity modulated arc therapy using dynamic multileaf collimation: An alternative to tomotherapy. *Phys Med Biol.* 40(9): 1435–1449, 1995.
42. Yu, C X, Symons J M, Du M N, Martinez A A, Wong J W. A method for implementing dynamic photon beam intensity modulation using independent jaws and multileaf collimators. *Phys. Med. Biol.* 40: 769–787, 1995b.
43. Ma L, Boyer A L, Ma C M, Xing L. Synchronizing dynamic multileaf collimators for producing two-dimensional intensity modulated fields with minimum beam delivery time. in press, *Int J Radiat Oncol Biol Phys.* 1999.
44. Ma L, Boyer A L, Findley D O, Geis P B, Mok E. Application of a vido-optic beam imaging system for quality assurance of medical accelerators. *Phys Med Biol.* 43: 3649–3659. 1998.
45. Ma L, Boyer A L, Xing L, Ma C M. An optimized leaf-setting algorithm for beam intensity modulation using dynamic multileaf collimators. *Phys Med Biol.* 43: 1629–1643. 1998.
46. Ma L, Geis P B, Boyer A L. Quality assurance for dynamic multileaf modulated fields using a fast beam imaging system. *Med Phys.* 24: 1213–1220, 1997.
47. Ma L, Yu C X, Sarfaraz M. A new strategy for shaping static radiation fields using multileaf collimators. Submitted for publication in *Phys Med Biol.* 1999.

48. Ling C C, Chui C S, Jackson A, Kutcher G J, Leibel S, LoSasso T, Mohan R, Bortfeld T, Reinstein L, Spirou S, Wang X, Wu Q, Zelefsky M, Fuks Z. Conformal radiation treatment of prostate cancer using inversely-planned intensity modulated photon beams produced with dynamic multileaf collimation. *Int. J. Radiat. Oncol. Biol. Phys*, 35:721–730, 1996.

49. Leibel S A, Heimann R, Kutcher G J, Zelefsky M J, Burman C M, Melian E, Orazem J, Mohan R, Losasso T J, Lo H-C, Wiseberg H A, Chapman D S, Ling C C, Fuks Z. Three-dimensional conformal radiation therapy in locally advanced carcinoma of the prostate: preliminary results of a phase I dose-escalation study. *Int J Radiat Oncol Biol Phys*. 48:55–56, 1994.

50. Suit H, Westgate S J. Impact of improved local-control on survival. *Int J Radiat Oncol Biol Phys* 12: 453–458, 1986.

51. Hyodynmaa S, Gastafsson A, Brame A. Optimation of conformal electron beam therapy using energy- and fluence-modulated beams, *Med Phys*. 23: 659–666, 1996.

52. Lief E P, Larsson A, Humm J L. Electron dose profile shaping by modulation of a scanning elementary beam, *Med Phys*. 23: 33–44, 1996.

53. Asell M, Hyodynmaa S, Gustafsson A, Brahme A. Optimization of 3D conformal electron beam therapy in inhomogeneous media by concomitant fluence and energy modulation. *Phys Med Biol* 42(11): 2083–100, 1997.

54. Alasti H, Galbraith D M. Depth dose flattening of electron beams using a wire mesh bolus. *Med Phys*. 22(10): 1675–83, 1995.

55. Lief E P, Lo Y C, Humm J L. Electron wedges for radiation therapy. *Int J Radiat Oncol Biol Phys*. 40(1): 233–43, 1998.

56. Lief E P, Larsson A, Humm J L. Electron dose profile shaping by modulation of a scanning elementary beam. *Med Phys*. 23(1):33–44, 1996.

57. Klein E E. Modulated electron beams using multi-segmented multileaf collimation. *Radiother Oncol* 48(3): 307–11, 1998.

58. Bostick W H. Possible techniques in direct-electron-beam tumor therapy. *Phys Rev*. 77 564–565. 1950.

59. Bielajew, A F. The effect of strong longitudinal magnetic fields on dose deposition from electron and photon beams. *Med Phys*. 20(4) 1117–1179, 1993.

60. Nath R, Schulz R J. Modification of electron-beam dose distribution by transverse magnetic field. *Med. Phys*. 5: 226–230, 1978.

61. Paliwal B H, Wiley A L, Wessels B W, Choi M C. Magnetic field modification of electron-beam dose distributions in inhomogeneous media. *Med. Phys*. 5:404–408, 1978.

62. Whitmire D P, Bernard D L. Magnetic modification of the electron-dose distribution in tissue and lung phantoms. *Med Phys*. 5(5) 403–417, 1978.

63. Weinhous M S, Nath R, Shulz, R J. Enhancement of electron beam dose distributions by longitudinal magnetic fields: Monte Carlo simulations and magnet system optimization. *Med Phys*. 12(5) 598–603, 1985.

64. Hogstrom K R, Mills M D, Almond P R. Electron beam dose calculations. *Phys Med Biol* 26(3): 445–459, 1981.

65. Hogstrom K R, Mills M D, Meyer J A, Palta J R, Mellenberg D E, Meoz R T, Fields R S. Dosimetric evaluation of a pencil-beam algorithm for electrons employing a two-dimensional heterogeneity correction. *Int J Radiat Oncol Biol Phys*. 10:561–569, 1984.

66. Ma C M, Faddegon B A, Rogers D W O, Mackie T R. Accurate characterization of the Monte Carlo calculated electron beams for radiotherapy. *Med Phys*. 24:401–417, 1997.

67. Nelson R, Hirayama H, Rogers D W O. The EGS4 code system, Stanford Linear Accelerator Center Report SLAC-265 (SLAC, Stanford, Calif.) 1985.

68. Rogers D W O, Faddegon B A, Ding G X, Ma C M, Wei J, Mackie T R. BEAM: a Monte Carlo code to simulate radiotherapy treatment units. *Med Phys* 22:503–525, 1995.

While the invention has been described in detail, and with reference to specific embodiments thereof, it will be apparent to one of ordinary skill in the art that various changes and modifications can be made therein without departing from the spirit and scope thereof. The artisan will further acknowledge that the examples recited herein are demonstrative only and are not meant to be limiting.

I, the inventor, claim:

1. A device for generating helical electron beams, said device comprising:

a linear accelerator; and a tertiary collimating cone disposed downstream of the linear accelerator;

wherein the collimating cone output provides the helical electron beams.

2. The device of claim 1, said device comprising:

an electron source;

a dynamic energy compensator adjusting the energy of electrons emitted by said electron source, and a magnetic electron collimator collimating electrons processed by said dynamic energy compensator.

3. A device of claim 2, wherein said collimator directs the electrons to travel a helical path.

4. The device of claim 2, further comprising:

a location controller for controlling a location of said magnetic electron collimator.

5. The device of claim 2, wherein the magnetic electron collimator generates an axial magnetic field having a primary component in a direction parallel to a path of travel of said electrons.

6. The device of claim 5 further comprising:

at least one foil disposed upstream of said magnetic electron collimator.

7. The device of claim 6 further comprising:

a location controller wherein said location controller controls the location of said magnet.

8. A collimating cone in the device of claim 1, for use with a linear accelerator, said collimating cone capable of converting an electron beam generated by said linear accelerator into a helical electron beam, said collimating cone comprising:

a magnetic electron collimator.

9. The collimating cone of claim 8, further comprising:

a dynamic energy compensator disposed upstream of said magnetic electron collimator.

10. The collimating cone of claim 9, further comprising:

at least one multileaf collimator; and a primary collimator, wherein said multileaf collimator and said primary collimator are disposed upstream of said dynamic energy compensator.

11. A collimating cone according to claim 8, further comprising:

at least one foil; and wherein said magnetic electron collimator comprises at least one magnet with a primary component of magnetic field in a plane substantially parallel to the direction of propagation of the electron beam.

12. The collimating cone of claim 11, further comprising:
a location controller wherein said location controller can control the location of said magnet within said collimating cone.

13. A method for treating a patient having a tumor and in need of treatment, said method comprising:
irradiating the tumor in said patient with a helical electron beam.

14. A method for reducing the amount of radiation irradiating non-cancerous tissue during cancer radiation therapy, said method comprising:
generating a helical electron beam; and
radiating cancerous tissue with said helical electron beam.

15. A method for reducing the amount of radiation irradiating non-cancerous tissue during cancer radiation therapy of claim 14, wherein generating the helical electron beam comprises:
collimating an electron beam with an axial magnetic field having a primary component in a direction parallel to the direction of propagation of the electron beam.

16. The method of claim 15 wherein the cancer being treated is selected from at least one of breast cancer, melanoma, head and neck cancer, lymphoma, nasopharyngeal carcinoma, sarcoma in the extremities, and testicular cancer.

17. The method of claim 15 further comprising attenuating the electron beam.

18. The method of claim 15, wherein said electron beam is generated by emissions of electrons from a radioactive material.

19. The method of claim 18, wherein said emitted, modulated electrons have energy ranging between 0.5 MeV and 40 MeV.

20. The method of claim 18, wherein the shape of the field of the helical electron beam ranges between 0.01 $cm^2$ and 800 $cm^2$.

21. The method of claim 13, wherein a helical path of the helical electron beam approximates n+½ rotations of electrons in the electron beam, where n is an integer.

22. The method of claim 14, wherein a helical path of the helical electron beam approximates n+½ rotations of electrons in the electron beam, where n is an integer.

23. The device of claim 11, wherein the foil is formed from at least one of aluminum, beryllium and copper.

24. The method of claim 14, wherein the magnetic field is generated external to the person or animal subject to radiation therapy.

25. The device of claim 2 wherein the magnetic electron collimator comprises a coil generating a magnetic field having a primary component in an axial direction of said coil.

26. The device of claim 2 wherein one end of said coil disposed away from the electron source is open to free space.

27. The device of claim 2 wherein the magnetic electron collimator comprises a permanent magnetic material formed in a cylindrical form and electrons pass through said cylindrical form in an axial direction of said cylinder.

28. The device of claim 25 further comprising a collimator disposed within the coil.

29. The method of claim 24 wherein the magnetic field has a strength of 1 Tesla or less.

30. The device of claim 25 wherein the magnetic field has a strength of 1 Tesla or less.

31. The device of claim 2, wherein the magnetic electron collimator generates a magnetic field having a primary component parallel to a direction of travel of electrons processed by the dynamic energy compensator.

32. The device of claim 2, wherein the electron source comprises a linear accelerator, and said magnetic electron collimator is disposed downstream of the linear accelerator to receive an electron beam.

33. The cone of claim 8, wherein the magnetic electron collimator is disposed downstream of the linear accelerator to receive an electron beam.

34. The method of claim 15, wherein generating the electron beam further comprises disposing the axial magnetic field downstream of a linear accelerator.

* * * * *

UNITED STATES PATENT AND TRADEMARK OFFICE
CERTIFICATE OF CORRECTION

| | | |
|---|---|---|
| PATENT NO. | : 6,878,951 B2 | Page 1 of 1 |
| APPLICATION NO. | : 10/259561 | |
| DATED | : April 12, 2005 | |
| INVENTOR(S) | : Lijun Ma | |

It is certified that error appears in the above-identified patent and that said Letters Patent is hereby corrected as shown below:

Insert at Column 1, line 8 the heading --STATEMENT REGARDING FEDERALLY SPONSORED RESEARCH OR DEVELOPMENT--

Insert at Column 1, following the above heading --This invention was made with government support under Grant Number DAMD17-00-1-0323 awarded by the US Army. The government has certain rights in the invention.--

Signed and Sealed this
Thirteenth Day of March, 2012

David J. Kappos
*Director of the United States Patent and Trademark Office*